United States Patent [19]
Hansen, deceased
[11] Plant 5,210
[45] Mar. 27, 1984

[54] ALMOND × PEACH HYBRID ROOTSTOCK TREE (HANSEN 2168)

[75] Inventor: Carl J. Hansen, deceased, late of Citrus Heights, Calif., by Betty C. Hansen, successor

[73] Assignee: The Regents of the University of California, Berkeley, Calif.

[21] Appl. No.: 408,612

[22] Filed: Aug. 16, 1982

[51] Int. Cl.[3] ..... A01H 5/03
[52] U.S. Cl. ..... Plt./30
[58] Field of Search ..... Plt./30, 42

*Primary Examiner*—Robert E. Bagwill
*Attorney, Agent, or Firm*—Roger B. Webster

[57] ABSTRACT

An almond × peach hybrid rootstock tree which is large, vigorous, upright to vase-shaped with medium trunk and branches, and peach-like in appearance; densely foliated with large, thin, smooth, medium green leaves on vigorous shoots and medium size on spurs; the leaves having a crenate-serrate margin, medium length petiole, and usually reniform glands; blooms from half-hardy, medium size, plump, pubescent flower buds; the flowers being large and conspicuous with large, ovate petals slightly pink in bud but becoming white when open; and is a productive bearer of ovate, white-fleshed fruit (not useful to the clone) having a peach-like, reddish-brown, very hard stone with large ridges; the tree root system being adventitious and deep rooting with uniformly emerging roots which are large, straight, and outwardly and downwardly inclined.

3 Drawing Figures

BACKGROUND OF THE VARIETY

Field of the Invention

The inventor, Carl J. Hansen, in the conduct of an extensive plant breeding program, originated a substantial number of new and distinct plant varieties, and which included the present almond × peach hybrid rootstock tree. Such plant breeding program was undertaken by inventor, Carl J. Hansen, in the research and experimental plant nursery and orchards of the Department of Pomology at the University of California, Davis, Yolo County, Calif.

CLASSIFICATION OF THE VARIETY

The present variety of rootstock tree is embraced by Subclass 30, Plants, of the U.S. Patent Office Manual of Classification.

EXISTING VARIETIES

Among existing plant varieties known to inventor, Carl J. Hansen, and mentioned herein for the purpose of reference or comparison, are the following:

Almond Tree ("Almond B"), an unpatented chance seedling selected from a commercial orchard located near Ballico, Merced County, Calif.; Peach Tree ("Peach 1-8-2"), an unpatented selection of the Department of Pomology, University of California , Davis, Calif.;

Almond × Peach rootstock tree ("Hansen 536"), a selection of the Department of Pomology, University of California, Davis, Calif., and the subject of co-pending U.S. plant patent application Ser. No. 408,715, filed Aug. 16, 1982; Almond tree ("Nonpareil"), unpatented; and Plum tree ("Marianna"), unpatented.

ORIGIN OF THE VARIETY

The present varity of almond × peach hybrid rootstock tree was originated by inventor, Carl J. Hansen, in the aforesaid research and experimental plant nursery and orchards, as a cross—by hand pollination—between "Almond B" and "Peach 1-8-2", and was a selection from a seedling population of said cross; the selection having been made upon the ascertainment—under careful and continuing observation—that the present $F_1$ clone bore certain desirable characteristics for use as a rootstock.

ASEXUAL REPRODUCTION OF THE VARIETY

Subsequent to its origination and selection, as above, the present almond × peach hybrid rootstock tree was successfully asexually reproduced by inventor, Carl J. Hansen, in the aforesaid research and experimental plant nursery and orchards; the reproductions having been accomplished from hardwood cuttings, and, in maturity, in certain test plots in the aforesaid experimental orchards, said reproductions ran true, in all respects, to the original tree of the present variety. Vegetative reproduction of the variety has also been successfully accomplished from softwood cuttings under mist, and by budding.

SUMMARY OF THE VARIETY

The present variety of almond × peach hybrid rootstock tree is large, vigorous, upright to vase-shaped with medium trunk and branches, and peach-like in appearance; densely foliated with large, thin, smooth, medium green leaves on vigorous shoots and medium size on spurs; the leaves having a crenate-serrate margin, medium length petiole, and usually reniform glands; blooms from half-hardy, medium size, plump, pubescent flower buds; the flowers being large and conspicuous with large, ovate petals slightly pink in bud but becoming white when open; and is a productive bearer of ovate, white-fleshed fruit (not useful to the clone) having a peach-like, reddish-brown, very hard stone with large ridges; the tree root system being adventitious and deep rooting with uniformly emerging roots which are large, straight, and outwardly and downwardly inclined.

The present variety of almond × peach hybrid rootstock tree is more particularly characterized as follows:

The present variety, as a rootstock, has high vigor and more so than other rootstocks, such as almond or peach seedlings, or the Marianna plum. Further, because of its high vigor, the present variety—as a rootstock—is more tolerant to drought and growth in marginal soil; this especially in comaprison to peach seedlings and the Marianna plum, but probably not almond seedlings.

Additionally, as a rootstock, the present variety is (a) Immune to the two common forms of root-knot nematodes; to-wit, *Meloidygyne incognita acrita* and *M. javanica;*

(b) Although not wholly resistant to crown rot caused by excess water and *Phytopthora fungi,* the present variety is more tolerant than many other rootstock selections of hybrid populations tested;

(c) The present variety can be successfully reproduced, in high percentages (75%-90%) by hardwood cuttings treated with hormones, fungicide, and planting in a nursery in the Fall of the year under California conditions;

(d) The deep rooting of the variety provides excellent anchorage of the rootstock, better than the major rootstocks such as peach seedlings and the Marianna plum;

(e) In comparison, the present variety generally resembles the tree of the clonal rootstock Hansen 536 in appearance, but is slightly more vigorous, roots more consistently, and differs in having tree branches that are more green with less red color of the developing leaves and shoots.

BRIEF DESCRIPTION OF THE DRAWING

The drawing is an illustration, by photographic reproduction in color, and in one view, of a tree of the variety; in another view, flowers of the variety; and, in a still further view, the root system out of ground and cut from the tree.

DESCRIPTION OF THE VARIETY

The botanical details of the present new and distinct variety of almond × peach hybrid rootstock tree—with color definitions in common color terms—are as follows:

Tree:

*Size.*—Large.

*Vigor.*—Vigorous.

*Form.*—Upright to vase-shaped. Peach-like appearance, with a peach habit in that flowers are produced laterally on long, vigorous shoots.

*Hardiness.*—Half-hardy.

*Productivity.*—Tree bears large number of fruit which are not useful to the clone.

*Use.*—Rootstock, primarily for almond and peach, but Japanese plum and prune varieties are compatible. Not compatible to apricot.

*Root system.*—Deep rooting. Uniformly emerging. Adventitious with large, straight, outwardly and downwardly inclined roots providing good tree anchorage. Roots develop readily on hardwood cuttings.

Trunk:

*Size.*—Medium.

*Texture.*—Smooth-barked.

*Color.*—Grayish brown that develops prominent vertical striations or fissures.

Branches:

*Size.*—Medium.

*Texture.*—Smooth-barked.

*Color.*—Brown. Newly developing shoots in Spring are green with slightly reddish color. Young (one-year old) shoots are green with a reddish brown overcolor on exposed upper surface. Older shoots become brown-gray.

*Lenticels.*—Numerous. Conspicuous. Horizontal.

Leaves:

*Density.*—Dense.

*Size.*—Large (medium on spurs). Average length — 79 mm. (range 68 to 85 mm.). Average width — 28 mm. (range 25 to 30 mm.). Ratio of width to length — 1:2.8.

*Thickness.*—Thin.

*Texture.*—Smooth.

*Color.*—Medium green on vigorous shoots.

*Margin.*—Crenate-serrate.

*Petiole.*—Medium length. Average length — 21 mm. Ratio petiole to blade — 1:3.8.

*Glands.*—Usually reniform. Average number — usually 2 to 3, sometimes none, 1 or 4.

Flower buds:

*Size.*—Medium.

*Hardiness.*—Half-hardy.

*Form.*—Plump.

*Pubescence.*—Pubescent.

Flowers:

*Blooming period.*—Mid-February. About with or slightly earlier than the Nonpareil almond.

*Size.*—Large. Average — 35-40 mm. in diameter when fully open. Showy.

*Peduncle.*—Glabrous. Average length — 3 mm.

*Calyx.*—Green overlaid with red.

*Sepals.*—Usually green inside. Glabrous at base, becoming pubescent at lobes and margins.

*Petals.*—Large. Slightly pink in bud, but becoming white when flower fully open. Prominent red at base of petal, but fades with age. Average size — 18 × 14 mm. Round-ovate, with very slight emarginate indentation on apical end.

*Stamens.*—Average size — 8-14 mm, longer on outside. Light pink, fading to white with age, but retaining pink at base.

*Anthers.*—Yellow.

Pistils.—Very straight. Pubescent. Some undeveloped.

Fruit:

*Season of maturity.*—Ripens in August.

*Bearing.*—Productive but non-useful. Borne on long shoots similar to peach.

*Form.*—Tends to be ovate and intermediate in structure between peach and almond.

*Flesh.*—White. Red next to stone. Becomes soft and develops a suture which tends to split at maturity, but without separating completely from stone.

*Pubescence.*—Skin highly pubescent.

*Flavor.*—Astringent.

Stone:

*Form.*—Peach-like in appearance.

*Ridges.*—Large. Very hard.

*Color.*—Reddish-brown.

*Kernel.*—Inedible.

Resistance to Insects and Diseases: Immune to root-knot nematodes *Meloidygyne incognita acrita* and *M. javanica.* Some tolerance to iron chlorosis.

The herein described almond × peach hybrid rootstock tree may vary in slight detail due to climatic and soil conditions under which the variety may be grown; the present description being of the variety as grown in the Central Valley of California.

It is claimed:

1. A new and distinct variety of almond × peach hybrid rootstock tree substantially as illustrated and described, particularly characterized by a high percentage of successful reproductions from hardwood cuttings, by a deep rooting, adventitious root system providing excellent anchorage, by immunity to root-knot nematode infections, *Meloidygyne incognita acrita* and *M. javanica*, and by a tree generally resembling the Hansen 536 but slightly more vigorous, roots from cuttings more consistently, and with tree branches which have more green and less red color of the developing leaves and shoots.

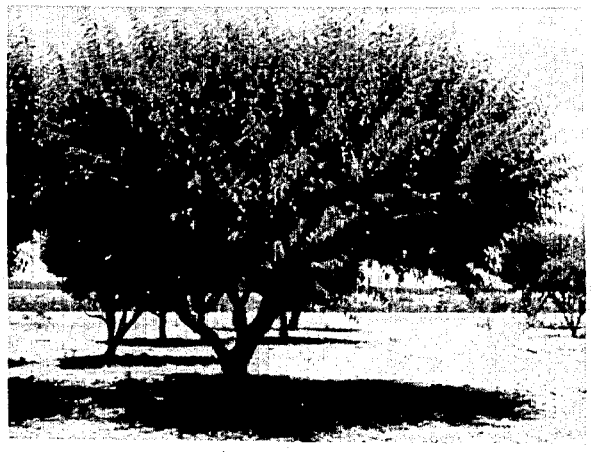
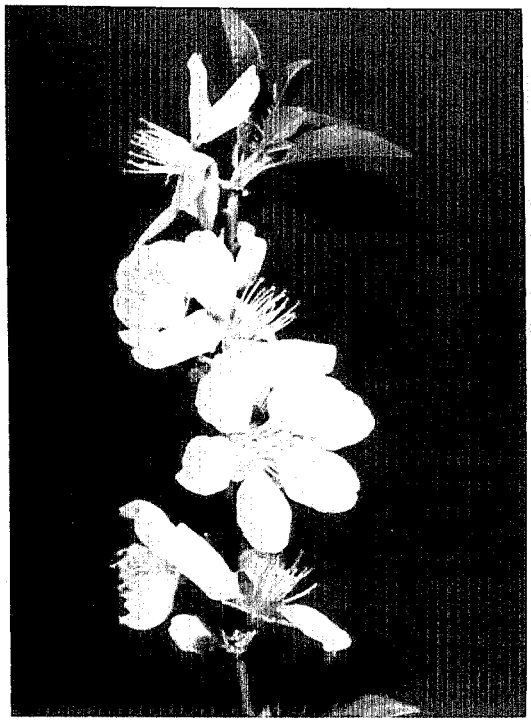
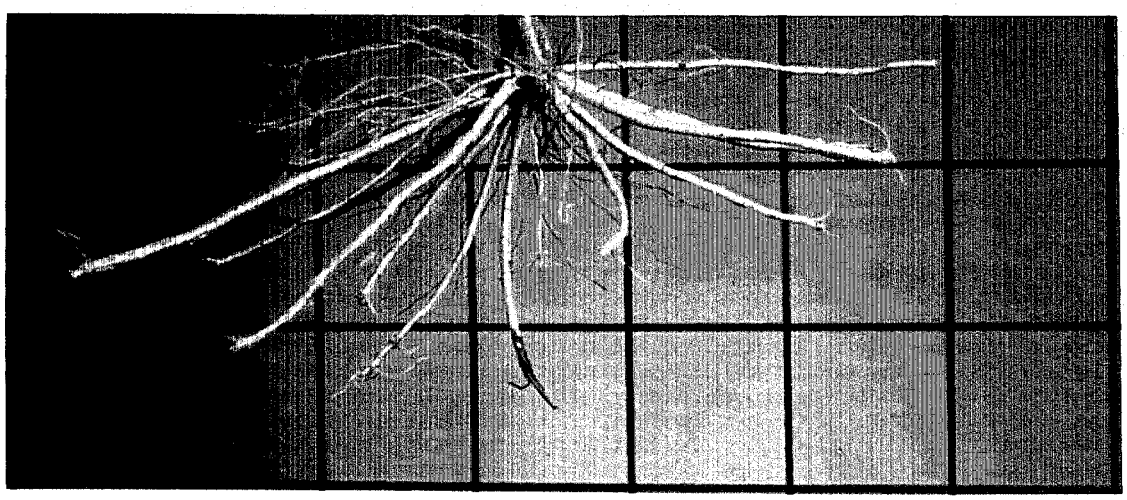

* * * * *